(12) United States Patent
Patrick et al.

(10) Patent No.: US 6,454,931 B2
(45) Date of Patent: *Sep. 24, 2002

(54) METHOD FOR MEASURING COMPONENT OF A GASEOUS EMISSION

(75) Inventors: Ronald S. Patrick, Mountain View, CA (US); Fabio DeAmicis, Los Altos, CA (US)

(73) Assignee: ECM Engine Control and Monitoring, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/819,229

(22) Filed: Mar. 27, 2001

Related U.S. Application Data

(63) Continuation of application No. 08/902,552, filed on Jul. 29, 1997, now Pat. No. 6,254,750.

(51) Int. Cl.[7] .............................................. G01N 27/407
(52) U.S. Cl. .................... 205/781; 204/425; 204/426; 205/784; 205/784.5; 205/788
(58) Field of Search ................................ 204/421–429; 205/781, 783.5–785, 788

(56) References Cited

U.S. PATENT DOCUMENTS

| 4,306,957 A | 12/1981 | Ishitani et al. ............... 204/195 |
| 4,769,124 A | 9/1988 | Okada et al. ................ 204/425 |
| 4,770,760 A | 9/1988 | Noda et al. .................. 204/425 |
| 4,927,517 A | 5/1990 | Mizutani et al. ............. 204/406 |
| 5,288,375 A | 2/1994 | Logothetis et al. ..... 204/153.18 |
| 5,643,429 A | 7/1997 | Wachsman ................... 205/781 |
| 5,672,811 A | 9/1997 | Kato et al. .................. 73/31.05 |
| 5,780,710 A | 7/1998 | Murase et al. ................ 73/1.06 |
| 5,879,525 A | * 3/1999 | Kato |
| 5,972,186 A | 10/1999 | Takeuchi et al. ............. 204/434 |
| 5,980,728 A | 11/1999 | Farber et al. ................ 205/784 |
| 6,171,470 B1 | * 1/2001 | Patrick et al. |
| 6,228,252 B1 | * 5/2001 | Miyata et al. |
| 6,254,750 B1 | * 7/2001 | Patrick et al. |

FOREIGN PATENT DOCUMENTS

GB 2 288 873 11/1995 ......... G01N/27/417

* cited by examiner

Primary Examiner—T. Tung
(74) Attorney, Agent, or Firm—Kenta Suzue; Wilson Sonsini Goodrich & Rosati

(57) ABSTRACT

A modified universal exhaust gas oxygen sensor, referred to herein as a CEGA sensor, is provided which can be used to measure the concentration of a variety of components of a gaseous fuel emission including CO, $CO_2$, $O_2$, $H_2$, and $H_2O$. The CEGA sensor employs at least one additional electrode on a ceramic substrate which possess a different catalytic activity relative to the electrodes that normally found on a UEGO sensor. The ceramic substrate may be made of any suitable ceramic and is preferably made of zirconia. The difference in catalytic activity between the additional electrode(s) and the electrodes native to the UEGO sensor create an oxygen gradient which enables a measure of combustion completeness to be calculated. In combination with an air/fuel ratio measured by the sensor, the concentrations of different components in the emission can be calculated. Several methods, devices and systems which can be used with various types of ceramic sensors including a CEGA sensor in order to improve their performance are also provided.

21 Claims, 14 Drawing Sheets

METHOD FOR MEASURING COMPONENT OF A GASEOUS EMISSION

This application is a continuation of application Ser. No. 08/902,552, filed Jul. 29 1997, now U.S. Pat. No. 6,254,750, which is incorporated herein by reference in its entirety.

FIELD OF THE INVENTION

The present invention relates to sensors for use in detecting gaseous components and more particularly to ceramic sensors for use in analyzing combustion emission components.

BACKGROUND OF THE INVENTION

A variety of sensors have been developed for detecting different gaseous combustion emission components. Examples of the different gaseous components which these sensors can detect include, but are not limited to oxygen ($O_2$), carbon monoxide (CO), carbon dioxide ($CO_2$), hydrocarbons (HC), and nitrogen oxides ($NO_x$). These sensors can be used in a variety of devices including, for example, automotive engines, diesel engines, gas turbine engines, jet engines, power plants, furnaces, and barbeques. Many of these gaseous components are hazardous.

Information derived from these sensors can be used for a variety of purposes. Data from the sensors can be used for feedback control of different aspects of a device which is producing a gaseous emission. Alternatively, these sensors can simply be used to monitor the content of the emission. For example, these sensors can be used as a component of an on-board, OEM emissions control system for an automotive engine or as an off-board emissions measuring device used for inspection and maintenance, for example as a tool for an automotive mechanic.

A need exists for sensors which can detect a wide array of gaseous components. For example, a need exists for a sensor which can determine the concentrations of oxygen, carbon monoxide, carbon dioxide, hydrocarbons, and nitrogen oxides in a sample. The sensors should have a high signal-to-noise ratio and thus be able to accurately determine the concentrations of various components of a gaseous sample. The sensors should be simple, reliable, and inexpensive to manufacture. These and other objectives are provided by the sensors, devices, and methods of the present invention.

SUMMARY OF THE INVENTION

The present invention relates to a modified universal exhaust gas oxygen sensor, referred to herein as a CEGA sensor, which can be used to measure the concentration of a variety of components of a gaseous emission including CO, $CO_2$, $O_2$, $H_2$, and $H_2O$. The CEGA sensor employs at least one additional electrode on a ceramic substrate which possess a different catalytic activity relative to the electrodes that are normally found on a UEGO sensor. The ceramic substrate may be made of any suitable ceramic and is preferably made of zirconia.

The difference in catalytic activity between the additional electrode(s) and the electrodes native to the UEGO sensor create an oxygen gradient which enables a measure of combustion completeness to be calculated. Combustion completeness is a parameter quantifying the degree to which the gaseous emissions of combustion are in chemical equilibrium. In combination with an air/fuel ratio measured by the sensor, the concentrations of different components in the emission can be calculated.

A method is also provided for measuring concentrations of components of a gaseous emission by measuring an air/fuel ratio using a ceramic sensor, measuring combustion completeness using the ceramic sensor and determining concentrations of components of a gaseous emission based on the measured air/fuel ratio and measured combustion completeness. The CEGA sensor of the present invention enable these functions of the method to be performed by a single sensor.

In one regard, the CEGA sensor is an improved universal exhaust gas oxygen sensor (UEGO) for measuring properties of a gaseous emission which includes at least one oxygen pumping cell and a sensing cell in contact with a detection cavity, the sensing cell including a ceramic in gas communication inside the detection cavity, a first electrode in contact with ceramic positioned inside the detection cavity, and a second electrode in contact with the other side of the ceramic, a first voltage potential externally applied between the first and second electrodes for pumping oxygen across the ceramic into and out of the detection cavity, the first voltage potential controlled by a second voltage potential formed across a third and fourth electrode of the sensing cell, an air/fuel ratio measurement of the gaseous emission being obtainable from the current passing between the first and second electrodes, the improvement comprising the addition of a fifth electrode which has a different catalytic activity than the first electrode positioned inside the detection cavity in contact with the pumping cell ceramic, a third voltage potential externally applied between the fifth electrode and either the second electrode or a sixth electrode located on the same side of the pumping cell ceramic as the second electrode, the third voltage potential controlled by a fourth voltage potential formed between the first and fifth electrodes, a measure of combustion completeness being obtainable from the current passing between the first and sixth electrodes.

In one particular embodiment of a CEGA sensor, the sensor includes a detection cavity;

a diffusion passage across which the gaseous emission enters the detection cavity; an oxygen pumping cell defining a portion of the detection cavity formed of a ceramic substrate and a first electrode in the detection cavity and a second electrode outside the detection cavity for pumping oxygen into and out of the detection cavity across the ceramic substrate to maintain a target oxygen level concentration in the detection cavity, an air/fuel ratio measurement of the gaseous emission being obtainable from current passing between the first and second electrodes; and a sensing cell defining a portion of the detection cavity formed of a ceramic substrate, the sensing cell including a third electrode within the detection cavity, a fourth electrode outside the detection cavity, a second voltage potential being formed between the third and fourth electrodes due to a difference in oxygen concentration across the third and fourth electrodes, and a fifth electrode in contact with the ceramic within the detection cavity which has a different catalytic activity than the first electrode, a forth voltage potential being formed between the fifth electrode and the first electrode, a measure of combustion completeness being obtainable from a current passing between the fifth and sixth electrodes.

The present invention also relates to several methods, devices and systems which can be used with various types of ceramic sensors including the CEGA sensor of the present invention in order to improve their performance.

In one regard, the invention relates to a method for calibrating a ceramic sensor which, as one of its functions, determines an air/fuel ratio. This method can be used in combination with any sensor which calculates an air/fuel ratio including, but not limited to UEGO, $NO_x$ and CEGA sensors.

According to the method, a ceramic sensor is operated at a constant, known air/fuel ratio. While being operated at a constant, known air/fuel ratio, the pumping current ($I_{pm}$) of the sensor is measured. A basic relationship which correlates the air/fuel ratio to the pumping current for the family of sensors to which the specific ceramic sensor belongs is then used to calibrate the sensor by comparing the measured pumping current ($I_{pm}$) to the expected pumping current from the basic relationship for that air/fuel ratio ($I_p$). A transformation between the measured pumping current ($I_{pm}$) and the current that the basic relationship gives for a known air/fuel ratio is created. During subsequent sensor usage, this transformation is used to modify the measured pumping current to create a value which is used with the basic relationship to obtain an air/fuel ratio that is accurate for the specific sensor.

In one particular embodiment, the method for calibrating a ceramic sensor which, as one of its functions, determines an air/fuel ratio includes the steps of:

operating the ceramic sensor at a constant, known air/fuel ratio;

measuring a pumping current of the sensor;

comparing the measured pumping current to an expected pumping current for the constant, known air/fuel ratio; and calibrating the sensor using a basic relationship which provides the expected pumping current for the air/fuel ratio at which the ceramic sensor was operated.

The present invention also relates to a software algorithm which can be incorporated into a system in which the sensor is used which compares $I_{pm}$ versus $I_p$ for one or more air/fuel ratios and produces a look-up table for $I_{pm}$ versus air/fuel ratio which can be used during the operation of the sensor.

The present invention also relates to a semiconductor memory device which can be used in combination with or incorporated into a ceramic sensor, the memory device including logic and data for performing a variety of functions. For example, the memory device can include logic for calibrating the sensor as well as memory for calibration data for the sensor. The memory device can also include logic and memory for storing usage information regarding the sensor. The memory device can also include logic which monitors and controls the operation of the sensor. The memory device can also include logic for detecting when the sensor is being used or has been used beyond its recommended limits, e.g., temperature, time, voltage, etc. The memory device can also include a mechanism for warning the user of the improper use or overuse.

A method is also provided for correcting for temperature transients by measuring the temperature of the sensor; and correcting an output of the sensor based on the measured temperature. The system for operating the sensor can also include logic for adjusting the sensor's output based on a determination of the sensor's temperature.

The present invention also relates to a method for reducing noise from leakage current from the sensor's heater by taking measurements when the heater is off or after the effects of the leakage current have reached steady-state, most preferably just prior to turning the heater on.

The present invention also relates to a method for reducing noise due to coupling between the heater wires and sensing element's wires by taking sensor measurements before transitions in the heater's voltage occur.

The present invention also relates to a method for reducing noise due to the use of a sensor impedance measuring method for determining a sensor's temperature by taking measurements just before the impedance measuring event.

The present invention also relates to logic for performing any of the above methods for avoiding noise by controlling when sensor measurements are taken. The present invention also relates to logic for determining whether the heater duty cycle is low or high and for selecting the measurement times based on the duty cycle.

The present invention also relates to a method for reducing noise due to a regulated voltage-type heater in a ceramic emission sensor system by measuring the noise due to the regulated voltage-type heater at and subtracting the noise from the sensor signals in order to compensate for this source of noise.

The present invention also relates to a method for improving the accuracy of measuring oxygen-containing species in a gaseous emission in multiple cavity sensors.

According to one embodiment, the method is performed by applying a gaseous emission to the sensor; measuring a pumping current in a first cavity of the sensor which has a functional relationship to an air/fuel ratio of the gaseous emission; measuring a pumping current in a second cavity of the sensor which has a functional relationship to an amount of oxygen-containing species in the gaseous emission and the air/fuel ratio of the gaseous emission; and using a combination of the measured pumping currents of the first and second cavities to measure an amount of oxygen-containing species in the gaseous emission. This method can be incorporated into the sensor by incorporating logic and data for performing the method into the sensor.

The present invention also relates to a method for field calibrating sensors using gaseous emissions. According to one embodiment, the method of field calibration is performed by applying a gaseous emission having a known amount of oxygen-containing species to the sensor; measuring a pumping current in a first cavity of the sensor which has a functional relationship to an air/fuel ratio of a model gas; measuring a pumping current in a second cavity of the sensor which has a functional relationship to the amount of oxygen-containing species in the gaseous emission and the air/fuel ratio of the gaseous emission; and using a combination of the measured pumping currents of the first and second cavities and the known amount of oxygen-containing species in the gaseous emission to calibrate the sensor. This method can be incorporated into the sensor by incorporating logic and data for performing the method into the sensor.

The present invention also relates to a method for minimizing the effect of rapid emission composition transients on the accuracy of multi-cavity exhaust sensors. According to the method, the effect of rapid emission composition transients on the accuracy of a multi-cavity exhaust sensor is minimized by measuring the sensor values; detecting for an occurrence of a rapid emission composition transient; discontinuing usage of the measured sensor values when the rapid emission composition transient is detected; detecting for a subsidence in the rapid emission composition transient; and resuming usage of the measured sensor values when subsidence of the rapid emission composition transient is detected.

BRIEF DESCRIPTION OF THE DRAWINGS

FIG. 10A illustrates a noiseless signal ($I_{p2}$) in the sense that extraneous noise has been eliminated.

FIG. 10B illustrates the duty cycling of voltage to the heater.

FIG. 10C illustrates how the signal illustrated in FIG. 10A is modified as a result of the leakage current.

FIG. 10C illustrates how the signal illustrated in FIG. 10A is modified as a result noise generated due to coupling between the heater wires and sensing element's wires.

FIG. 10D illustrates the noise effects associated with the signal illustrated in FIG. 10B.

FIG. 10E illustrates the noise effect associated with the timing of a sensor impedance measurement.

FIG. 10F illustrates a low heater duty cycle.

FIG. 10G illustrates a signal with noise generated from a heater operating with a low heater duty cycle.

FIG. 10H illustrates a high heater duty cycle.

FIG. 10I illustrates a signal with noise generated from a heater operating with a high heater duty cycle.

DETAILED DESCRIPTION OF PREFERRED EMBODIMENTS

Figure 1:
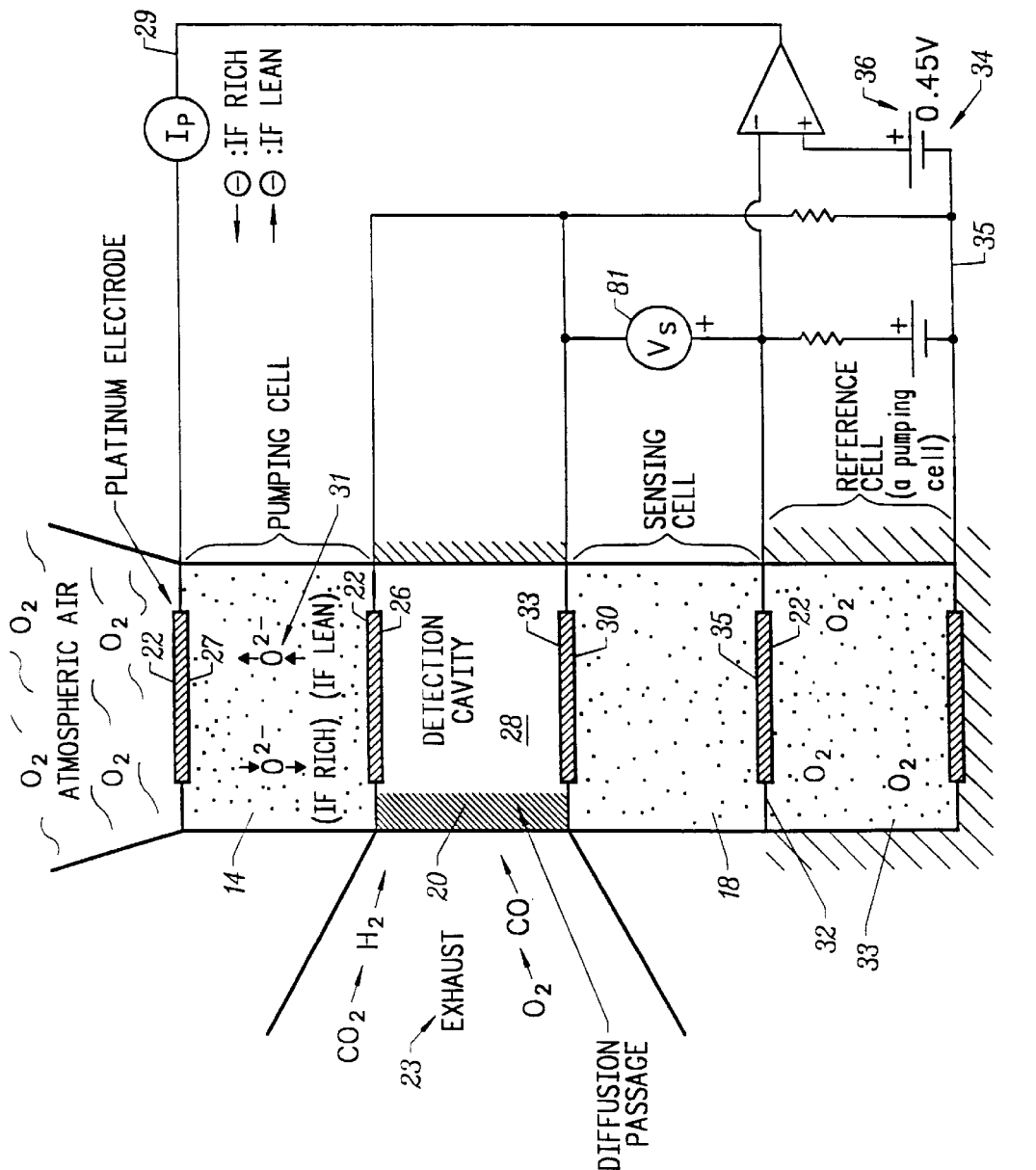
FIG. 1 illustrates an embodiment of an UEGO sensor.

The present invention relates to a modified universal exhaust gas oxygen (UEGO) sensor which can be used to measure the concentration of a variety of components of a gaseous fuel emission including CO, $CO_2$, $O_2$, $H_2$, and $H_2O$. The modified UEGO sensor, referred to herein as a CEGA sensor, has an analogous structure to a UEGO sensor but employs at least one additional electrode on the ceramic substrate which possess a different catalytic activity relative to the electrodes that normally found on a UEGO sensor. The ceramic substrate may be made of any suitable ceramic and is preferably made of zirconia.

The difference in the catalytic activity between the one or more additional electrodes in the CEGA sensor and the electrodes native to a UEGO sensor causes an $O_2$ gradient to be formed when the emission is not in chemical equilibrium due to an excess of either $O_2$ consuming or $O_2$ generating reactions occurring in the vicinity of the electrode with a higher catalytic activity. By monitoring the size of the $O_2$ gradient, a measure of combustion completeness can be calculated. The CEGA sensor, like a UEGO sensor, is able to measure an air/fuel ratio. By comparing the combustion completeness and air/fuel ratio measurements, the concentrations of different components in the emission can be calculated.

The present invention also relates to several devices, methods and systems which can be used with various types of ceramic sensors including the CEGA sensor of the present invention in order to improve their performance.

1. EGO, UEGO & $NO_x$ Type Ceramic Sensors

A variety of different ceramic gas sensors have been developed for detecting different products in combustion emission components. These ceramic sensors can include a variety of ceramic substrates including, for example, zirconia ($ZrO_2$) and titania. One type of ceramic gas sensor that has been developed is the exhaust gas oxygen sensor (EGO). These sensors are used to maximize the efficiency of a catalytic converter which receives the emissions. For maximum converter efficiency, it must be fed with emissions from combustion processes operating at a stoichiometric balance between air and fuel. EGO sensors can only detect whether an engine is running rich or lean of the stoichiometric point. The voltage potential ($V_s$) generated by an EGO sensor can be expressed according to the following equation:

$$V_s = (RT/4F) \ln(Po_2 1 / Po_2 2) \qquad (I)$$

where:
R is the gas constant;
T is the temperature;
F is the Faraday constant;
$Po_2 1$ is the partial pressure of oxygen on side 1 of the sensing cell exposed to the combustion emissions; and
$Po_2 2$ is the partial pressure of oxygen on side 2 of the sensing cell exposed to a reservoir of oxygen molecules of a known concentration.

Equation I has a very sharp transition value at the stoichiometric point and hence can be used to identify this point. The sensor can also be used to measure oxygen concentrations of the emission in the vicinity of the stoichiometric point. While EGO sensors can detect whether an engine is operating at, above or below the stoichiometric point, the sensor cannot detect the actual air/fuel ratio of the emission.

A second type of ceramic gas sensor that has been developed is the universal exhaust gas oxygen sensor (UEGO). Unlike the EGO, UEGO sensors are "linear" oxygen sensors in the sense that they can detect the actual air/fuel ratio of the emission.

FIG. 1 illustrates an embodiment of an UEGO sensor. As illustrated, the sensor includes three ceramic cells 14, 18, 33 and a porous diffusion passage 20 into which emissions 23 enter the sensor. Two of the ceramic cells 14, 33 are used for pumping oxygen while the third cell 18 is used as a sensing cell.

All three ceramic cells have platinum electrodes 22 attached to each side of the ceramic substrate. When a voltage potential is placed across the pumping cell's electrodes and the cell's temperature is above 300° C., oxygen is pumped through the ceramic from one side 26 (or 27) of a cell to another side 27 (or 26) of the cell via the chemical reaction:

$$O_2 + 4e^- \leftrightarrows 2O^{2-} \tag{II}$$

The oxygen ions 31 generated during pumping pass through the ceramic while the electrons travel through external circuitry 29 connecting the electrodes. The amount of oxygen that is pumped through the cell is detected by the external circuitry by measuring the amount of current generated, four electrons equaling a pumped oxygen molecule.

Sensing cell 18 is an EGO sensor which generates a voltage potential ($V_s$) across electrodes 33, 35 when a difference in oxygen concentration is present across its surface. The voltage potential ($V_s$) is used to drive external circuitry 29 whose purpose is to pump oxygen into and out of the detection cavity 28 so as to maintain a stoichiometric exhaust composition therein.

The diffusion passage 20 allows combustion constituents to flow into and out of a detection cavity 28 located between one of the pumping cells 14 and the sensing cell 18. Overtime, the composition of components on either side of the diffusion passage would be equal if not for the pumping of oxygen into and out of the detection cavity 28 by the pumping cell 14 and the combustion reactions that occur inside the detection cavity 28. By measuring the amount of oxygen pumped via the external current flow ($I_p$) into or out of the detection cavity 28 to maintain a stoichiometric exhaust composition, the exhaust's air/fuel ratio is determined.

When the exhaust mixture contains excess oxygen relative to a stoichiometric air/fuel ratio, commonly referred to as lean of stoichiometric, oxygen from the exhaust diffuses through the passage into the detection cavity 28. In this case, the pumping cell 14 removes oxygen from the detection cavity 28 to create a stoichiometric exhaust composition.

When the exhaust mixture contains less oxygen relative to a stoichiometric air/fuel ratio, commonly referred to as rich of stoichiometric, CO and $H_2$ from the exhaust diffuse through the passage into the detection cavity 28. In this instance, the pumping cell 14 pumps oxygen into the detection cavity 28 which reacts with CO and $H_2$ to create a stoichiometric exhaust composition.

The sensing cell 18 has one side 30 exposed to the pumping cell 14 and another side 32 exposed to a reference cell 33 which has a constant oxygen concentration. In some embodiments, the reference cell is passive and is the environment outside the sensor. Alternatively, as illustrated in FIG. 1, the reference 33 cell can be an active type reference cell whose $O_2$ concentration is held constant via a small pumping current.

Also shown in FIG. 1 are pumping cell control electronics 35. The positive side 34 of an op-amp 36 is held at approximately 0.45 V (the $V_s$ target) and depending on whether the sensing cells voltage is >0.45 V (i.e., a rich mixture in the detecting cavity) or <0.45 V (i.e., a lean mixture in the detecting cavity) the op-amp 36 either supplies electrons (for rich mixtures) or removes electrons (for lean mixtures) from the reference cell 33. This results in $O_2$ either being supplied to the detection cavity for rich mixtures or removed from the detection cavity for lean mixtures.

Figure 2:
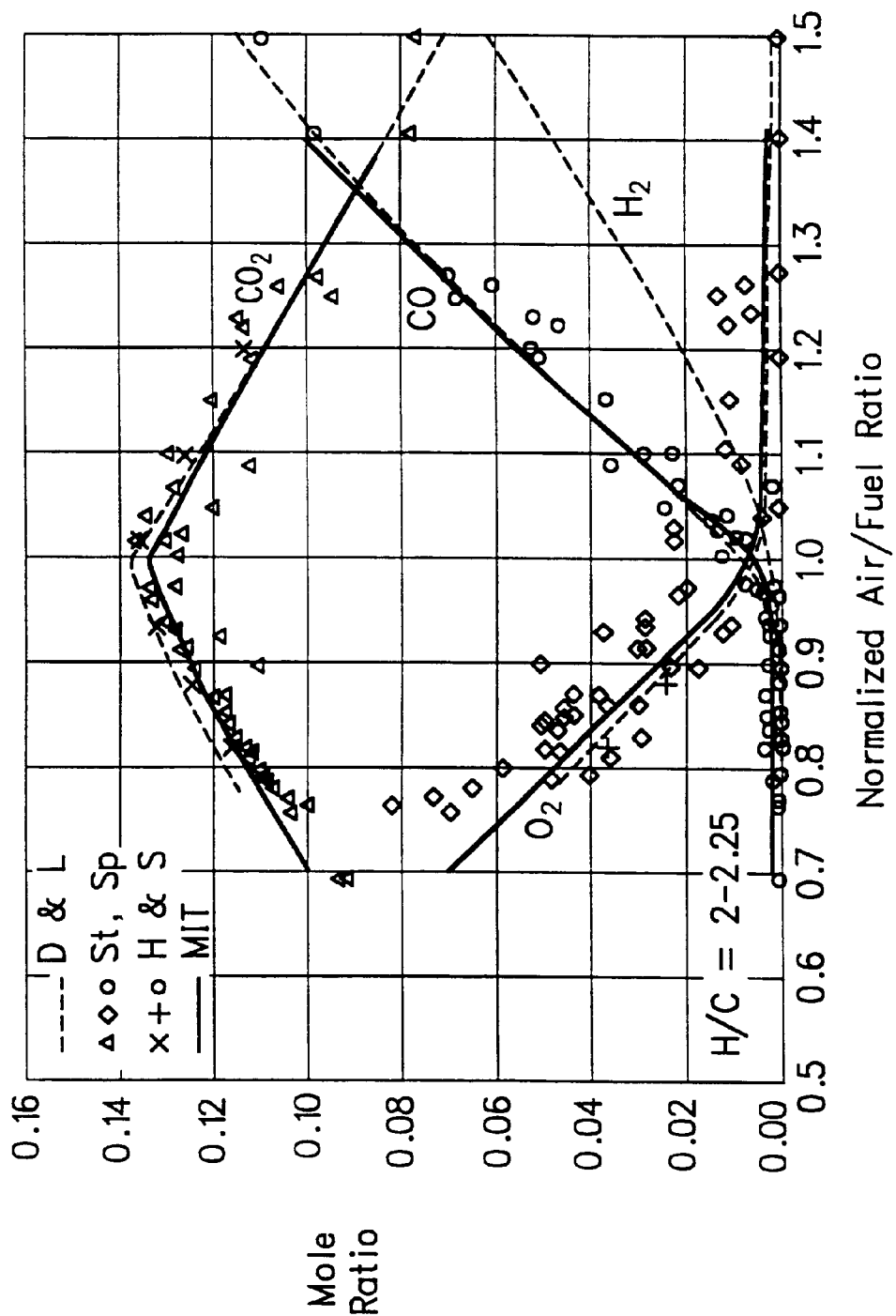
FIG. 2 provides a graph illustrating that the concentrations of CO, $CO_2$, $O_2$ and $H_2$ in an engine's exhaust are a function of the normalized air/fuel ratio.

The amount of oxygen pumped by the pumping cell 14 to balance the diffusion of $O_2$, CO, and $H_2$ into the detection cavity 28 is a function of the following parameters:

a) the diffusivity Of $O_2$ through the diffusion passage;
b) the diffusivity of CO through the diffusion passage;
c) the diffusivity of $H_2$ through the diffusion passage; and
d) the concentration of $O_2$, CO, and $H_2$ in the exhaust which is a function of the fuel's chemical composition (H:C and O:C ratios) and the air/fuel ratio, as illustrated in FIG. 2.

The diffusion coefficients are principally set by the structure of the diffusion passage. These coefficients can be determined by calibration instruments and are provided with the sensor. The fuel's composition (H:C and O:C ratios) can be input by the user. With this background information, the air/fuel ratio can be calculated.

A third type of ceramic sensor that has been developed is a $NO_x$ sensor. A $NO_x$ sensor is essentially an UEGO sensor with an additional diffusion passage and cavity. See U.S. Pat. No. 5,145,566. In addition to detecting the air/fuel ratio as does the UEGO sensor, the additional diffusion passage and cavity of the $NO_x$ sensor enables the detection of other emission components such as CO, $CO_2$, $H_2O$ and $NO_x$.

Figure 3:
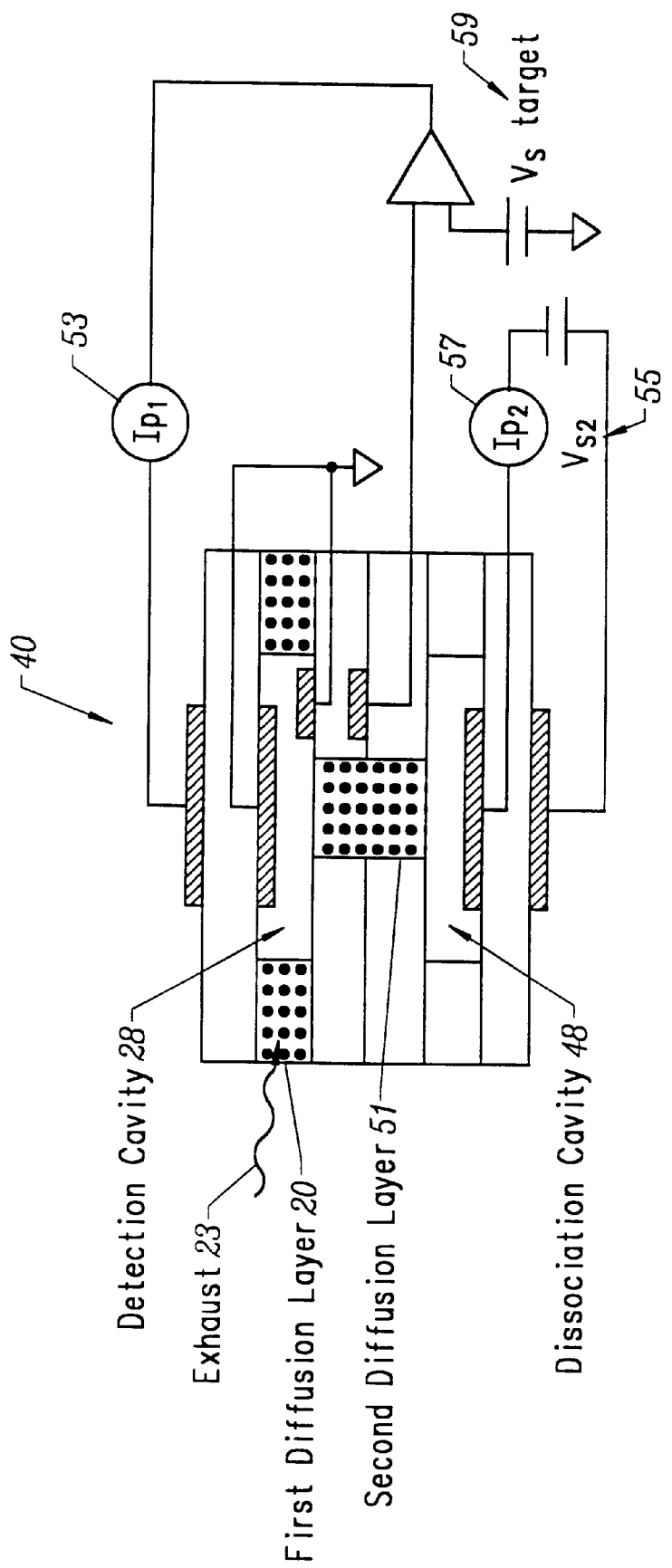
FIG. 3 illustrates an embodiment of a $NO_x$ sensor.

An embodiment of a $NO_x$ sensor is illustrated in FIG. 3. As illustrated in FIG. 3, the sensor 40 integrates a UEGO sensor with a second cavity 48.

The UEGO portion of the sensor 40, defined by first diffusion layer 20 and detection cavity 28, acts to keep the oxygen concentration of the detection cavity 28 at a low and constant amount by pumping oxygen into and out of the detection cavity 28. Combustion gases enter the detection chamber 28 via the first diffusion layer 20 as in a UEGO sensor. By monitoring the pumping current of the detection cavity ($I_{p1}$), oxygen concentrations and air/fuel ratios are measured.

Gases within the detection cavity 28 pass through a second diffusion layer 51 where they enter the dissociation cavity 48. In the dissociation cavity 48, a constant pumping potential is maintained which selectively strips oxygen from $NO_x$ molecules producing a dissociation cavity current $Ip_2$. The dissociation cavity current is proportional to the $NO_x$ concentration in the exhaust.

It is noted that although the $NO_x$ sensor is described with regard to the embodiment illustrated in FIG. 3, several other configurations of $NO_x$ known and/or possible and are intended to fall within the scope of this invention.

2. CEGA Sensors

A modified universal exhaust gas oxygen (UEGO) sensor which can be used to measure the concentration of a variety of components of a gaseous fuel emission including CO, $CO_2$, $O_2$, $H_2$, and $H_2O$ has also been developed. The modified UEGO sensor, referred to herein as a CEGA sensor, has an analogous structure to a UEGO sensor but employs one or more additional electrodes on the ceramic substrate which possess a different catalytic activity relative to the electrodes that are normally found on the ceramic substrate of a UEGO sensor.

The difference in the catalytic activity between the one or more additional electrodes in the CEGA sensor and the electrodes native to a UEGO sensor causes an $O_2$ gradient to be formed when the emission is not in chemical equilibrium due to an excess of either $O_2$ consuming or $O_2$ generating reactions occurring in the vicinity of the electrode with a higher catalytic activity. By monitoring the size of the $O_2$ gradient, a measure of combustion completeness can be calculated. The CEGA sensor, like a UEGO sensor, is able to measure an air/fuel ratio. By using the combustion completeness and air/fuel ratio measurements, the concentrations of different components in the emission can be calculated.

CEGA sensors provide advantages over existing ceramic sensors. For example, CEGA sensors are less complex to build and have a greater speed of response than the sensors described in U.S. Pat. No. 5,145,566 for measuring exhaust components including CO, $CO_2$, and $H_2O$.

Figure 4:
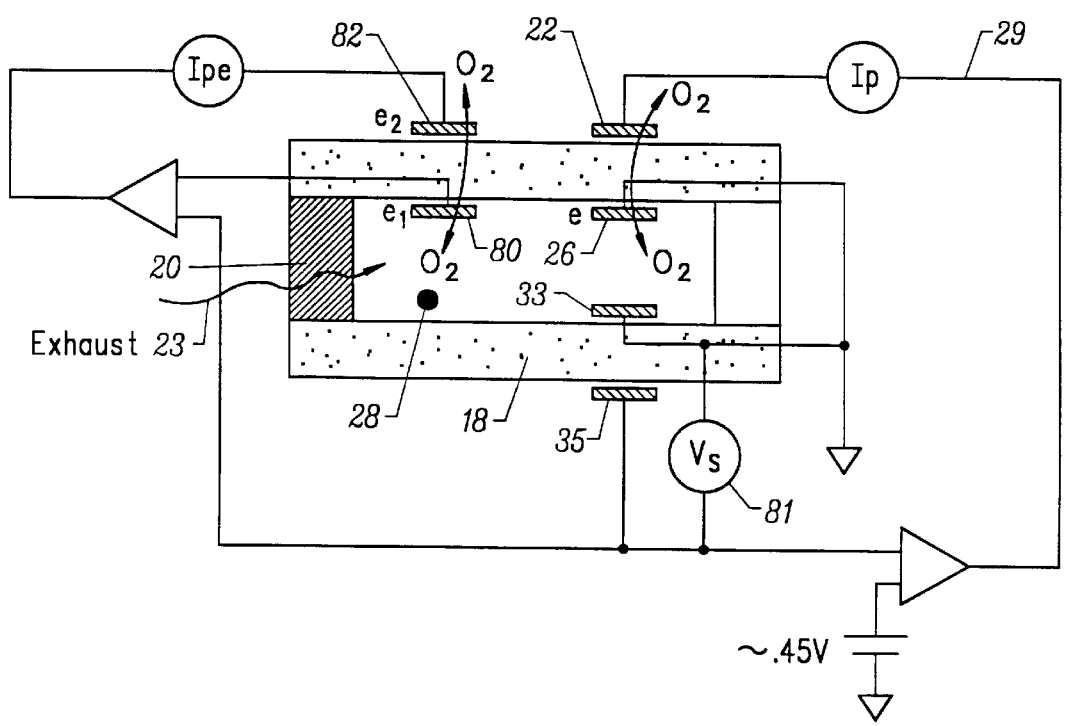
FIG. 4 illustrates an embodiment of a CEGA sensor with two additional electrodes relative to a UEGO sensor.
Figure 5:
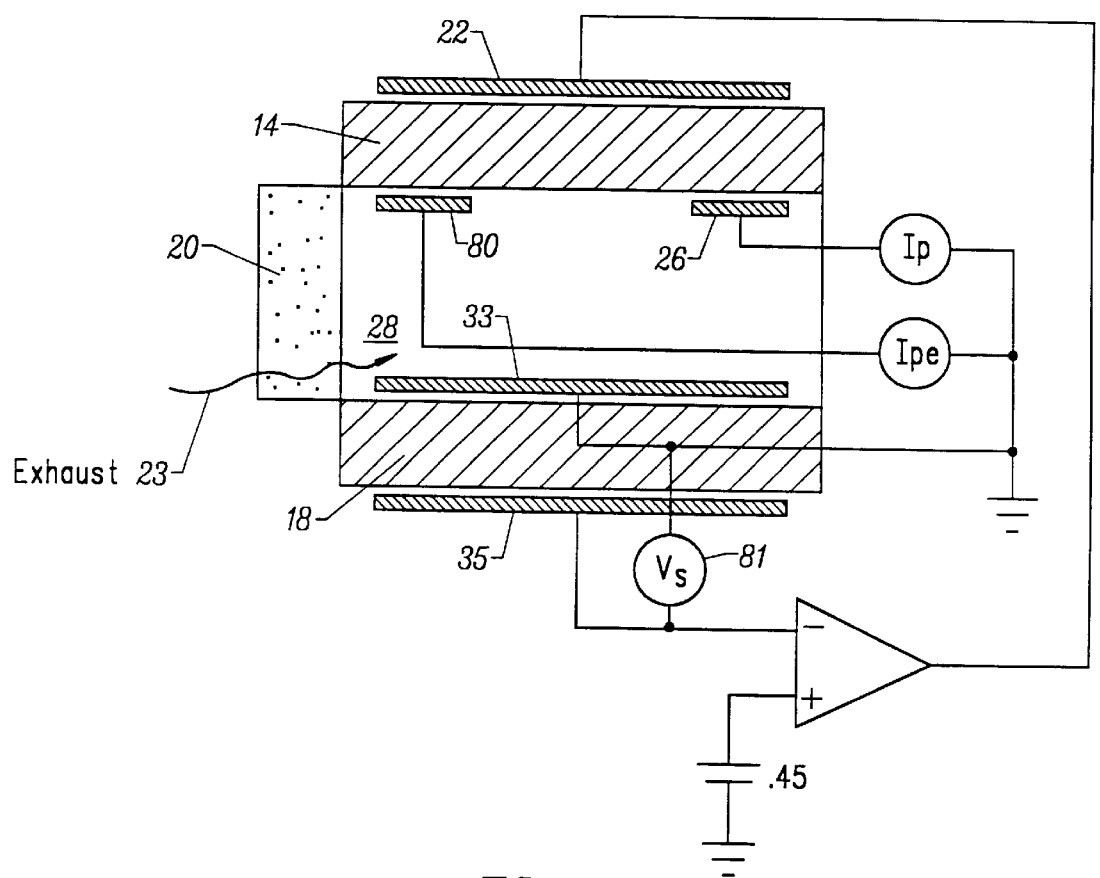
FIG. 5 illustrates an embodiment of a CEGA sensor with one additional electrode relative to a UEGO sensor.

Two embodiments of a CEGA sensor are illustrated in FIGS. 4 and 5. As illustrated, the CEGA sensor is essentially a wide-range UEGO sensor such as the sensor illustrated in FIG. 1 where one or more electrodes have been added. For example, the CEGA sensor illustrated in FIG. 4 has two additional electrodes 80 and 82. The CEGA sensor illustrated in FIG. 5 has one additional electrode 80.

With regard to FIGS. 4 and 5, the electrode 80 is positioned in the detection cavity 28 of the sensor on the same substrate as the pumping cell electrode 26. Electrode 80 has a different (more or less) catalytic activity than the pumping cell electrode 26. With regard to FIG. 4, the CEGA sensor also includes a second electrode 82 positioned outside of the detection cavity 28.

With regard to the CEGA sensor illustrated in FIG. 5, this CEGA sensor differs from the CEGA sensor illustrated in FIG. 4 in that it does not include electrode 82. Instead, another electrode which is used in the basic UEGO sensor, for example electrode 22, can perform the function otherwise provided by electrode 82.

The CEGA sensor pumps oxygen into and out of the detection cavity 28 to maintain a constant sensing cell voltage ($V_s$) 81 independent of the stoichiometry of the combustion device's exhaust 23 which enters the detection cavity 28 through diffusion aperture 20.

Electrodes 80 and 26 have different levels of catalytic activity. If the gas entering the detection cavity 28 is not in chemical equilibrium, these different levels of catalytic activity create a difference in the oxygen concentration between electrodes 80 and 26 which can be used to determine the degree of combustion completeness of the combustion device's exhaust.

The voltage potential between electrodes 26 and 80 created by the difference in oxygen concentrations can be used to drive external electronics whose purpose is to pump oxygen to or away from electrode 26 in order to reduce the voltage potential between electrodes 26 and 80. The polarity and amount of oxygen pumped is a function of the degree of combustion completeness of the exhaust gas entering the sensor and can be measured as a function of an oxygen pumping current ($I_{pe}$).

The chemical composition of the emission can be determined from the detected air/fuel ratio and degree of combustion completeness as described below. First the total pumping current ($I_p+I_{pe}$) is measured and used to determine the air/fuel ratio. Determination of the air/fuel ratio can be performed according as is known in the art with regard to UEGO sensors.

At any given air/fuel ratio, the percentage of component X can be represented by the equation:

$$Xi = Xi, afr + Gi, afr \times CC \qquad (III)$$

where: Xi is the mole fraction of exhaust component i;
Xi,afr is the mole fraction of component i realized in a combustion device with low combustion completeness;
Gi,afr is the difference between the mole fraction of component i realized in a combustion device with high combustion completeness and Xi,afr; and
CC is the degree of combustion completeness, 0 representing 0% combustion completeness. and 1 representing 100% combustion completeness.

As illustrated in FIG. 2, the chemical composition is a function of the air/fuel ratio. However, different compositions can exhibit the same air/fuel ratio. The fact that the air/fuel ratio does not uniquely determine the chemical composition of the emission has previously made it impossible to use an air/fuel ratio sensor as a chemical composition measuring device.

In a CEGA sensor, the degree of combustion completeness is determined in addition to the air/fuel ratio. By determining both the air/fuel ratio and degree of combustion completeness, this combination of measurements can be used to uniquely determine the chemical composition.

With regard to the CEGA sensor illustrated in FIG. 4, oxygen pumping current ($I_{pe}$) is measured across electrodes 26 and 82 and can be used to determine combustion completeness (CC) via the equation:

$$CC = CC_{MAX} - G_{CC} \times I_{pe} \qquad (IV)$$

where: $G_{CC}$ and $CC_{MAX}$ are determined by experimentation.

With regard to the CEGA sensor illustrated in FIG. 5, pumping current ($I_{pe}$) measured across electrodes 80 and 22 and can be used to determine combustion completeness (CC) via the equation:

$$CC = I_{pe}/I_p \qquad (V)$$

CEGA sensors provide several significant advantages over prior art air/fuel ratio sensors such as UEGO sensors. For example, CEGA sensors can be used to determine the chemical composition of an exhaust from a combustion device as well as the condition of an upstream catalytic converter, the condition of the catalytic converter being determined by placing the CEGA sensor downstream of the converter. If the catalytic converter is working effectively to bring the exhaust into chemical equilibrium, the potential between the electrodes 26 and 80 in the CEGA sensor will be small. In this regard, the CEGA sensor functions much like a second catalytic converter. Accordingly, if the potential between the electrodes 26 and 80 is small, this indicates that the first catalytic converter is effectively bringing the emissions into chemical equilibrium. By contrast, if the potential between the electrodes 26 and 80 is large, this indicates that the first catalytic converter is operating at less than 100% effectiveness. As a result, the effectiveness of the catalytic converter can be measured as a function of the $I_{pe}$.

Automotive manufacturers currently use two exhaust sensors to determine the condition of the catalytic converter, one upstream and one downstream of the catalytic converter. The stoichiometry of the engine is varied to give a sinusoidal signal to the sensor upstream of the catalyst. If the sensor downstream of the catalyst sees the same sinusoidal signal then the catalytic converter is not effective. The advantage of the described invention is that it removes the necessity of the exhaust sensor normally positioned upstream of the catalytic converter.

The present invention also relates to several methods for operating ceramic sensors as well as devices which can be used in combination with ceramic sensors which improve the performance of the sensors.

3. Method for Calibrating Air/Fuel Ratio Sensors

One embodiment of the present invention relates to a method for calibrating a ceramic sensor which, as one of its functions, determines an air/fuel ratio. This method can be used in combination with any sensor which calculates an air/fuel ratio including, but not limited to UEGO, $NO_x$, and CEGA sensors.

Figure 6:
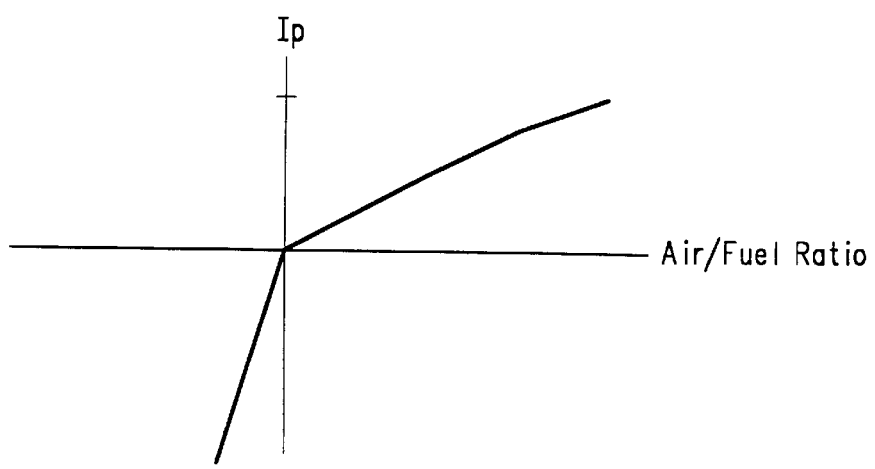
FIG. 6 illustrates the basic relationship between the pumping current ($I_p$) in a ceramic sensor and the air/fuel ratio.

In this embodiment, the accuracy of a ceramic sensor which determines an air/fuel ratio is improved by using a basic relationship between a pumping current ($I_p$) and an air/fuel ratio and modifying the use of that relationship to calibrate a specific sensor. FIG. 6 illustrates the basic relationship between the pumping current ($I_p$) in a ceramic sensor and the air/fuel ratio.

According to the method, a ceramic sensor is operated at a constant, known air/fuel ratio. While being operated at a constant, known air/fuel ratio, the pumping current ($I_{pm}$) of the sensor is measured. A basic relationship which correlates the air/fuel ratio to the pumping current, such as FIG. 6, is then used to calibrate the sensor by comparing the measured pumping current ($I_{pm}$) to the expected pumping current for that air/fuel ratio ($I_p$). A transformation between the measured pumping current ($I_{pm}$) and the current that the basic relationship gives for a known air/fuel ratio is created. During subsequent sensor usage, this transformation is used to modify the measured pumping current to create a value which is used with the basic relationship to obtain an air/fuel ratio that is accurate for the specific sensor.

A software algorithm can be used to compare $I_{pm}$ versus $I_p$ for one or more air/fuel ratios and produce a look-up table for $I_{pm}$ versus air/fuel ratio which can be used during the operation of the sensor.

This method has the advantage of being computationally simple, thus enabling the calibration to be performed quickly. Because the algorithm for performing this method is simple, a small amount of memory is needed to store the algorithm. In addition, the algorithm does not require detailed knowledge of the characteristics of the sensor.

4. Memory Device For Ceramic Sensors

This embodiment of the invention relates to a semiconductor memory device which can be used in combination with or incorporated into a ceramic sensor. The memory device can be used in a system which includes the sensor to control the sensor, calibrate the sensor, and/or monitor the sensor's usage and performance.

Figure 7:
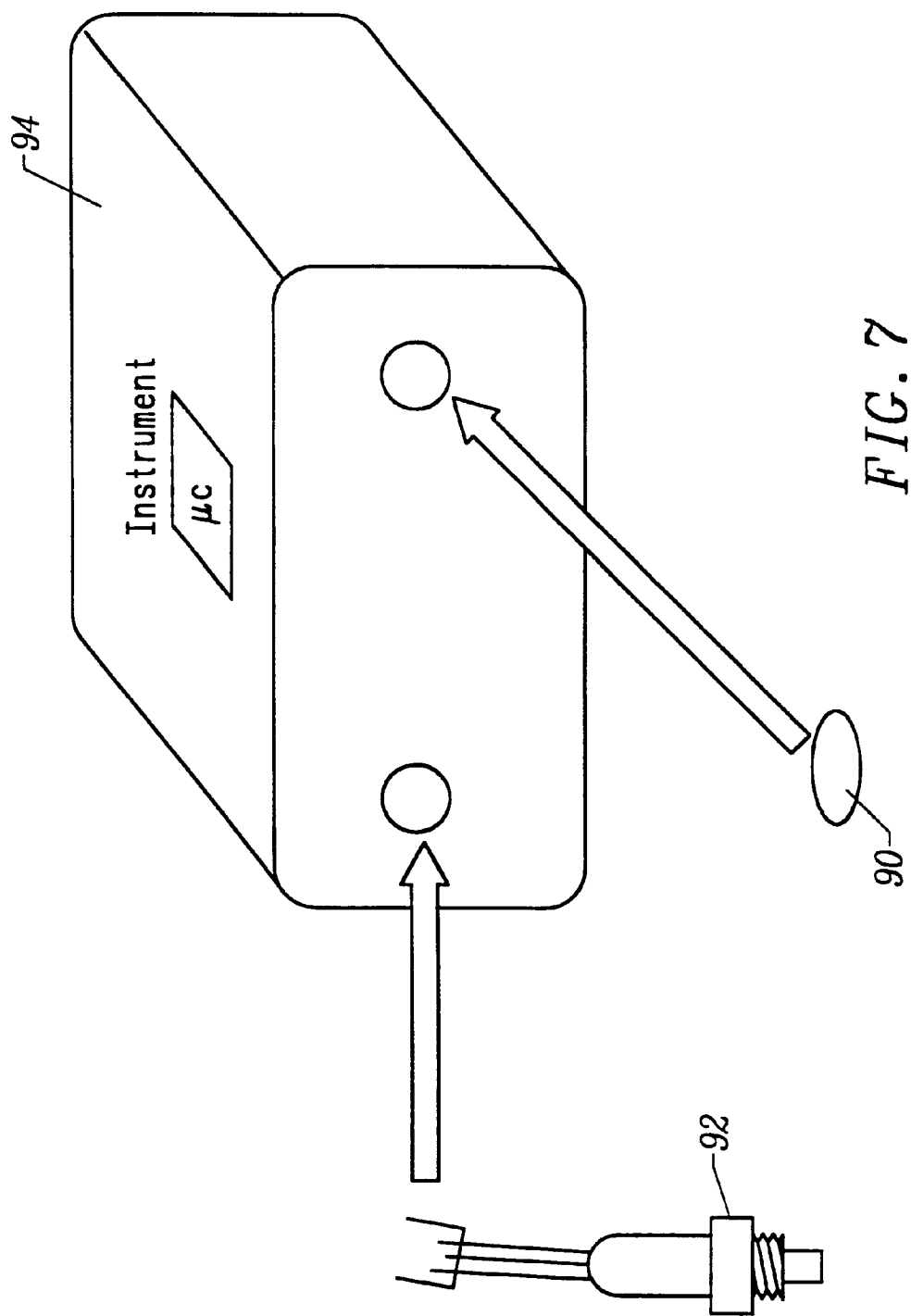
FIG. 7 illustrates an embodiment of a memory device coupled to a sensor in a system according to the present invention.

FIG. 7 illustrates an embodiment of a memory device coupled to a sensor in a system according to the present invention. As illustrated, the memory device 90 is designed to be attached to the gaseous component analyzer 94. The sensor is also attached to the analyzer.

Figure 8:
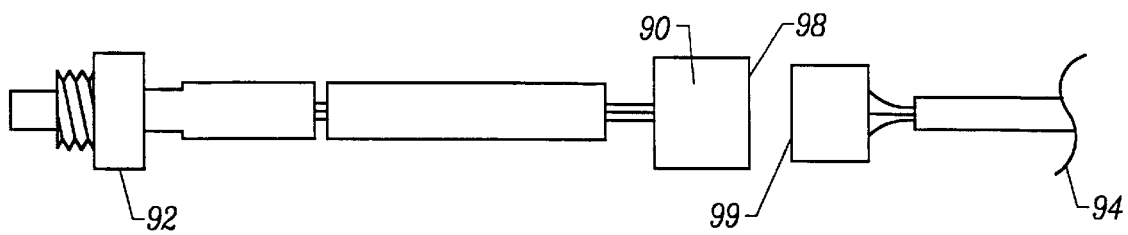
FIG. 8 illustrates an alternate embodiment where the memory device is built into the sensor.

FIG. 8 illustrates an alternate embodiment where the memory device 90 is built into the sensor 92. In this embodiment, the memory device 90 and sensor 92 have a single connector 98 which attaches to the analyzer 94 via connector 99.

The memory device can include logic for performing a variety of functions. For example, the memory device can include logic for calibrating the sensor. In addition, the memory device can include a look-up table for use with the logic to calibrate the sensor. By using a memory device in combination with a sensor, automated calibration of gas sensors can be performed.

For standardized quality control methodologies, it may be required that the user calibrate the sensor. Calibration is generally performed at a central location, after which the sensors are distributed to sites where they are used. The memory device of the present invention can include logic to store field calibration information which can be transferred from site to site as the sensor is used. By using the memory device in this manner, opportunity for calibration information loss or mistakes in its use are significantly reduced.

The memory device can also include logic and memory for storing usage information regarding the sensor. For example, the usage memory can be used to record the number of hours that the sensor has been used. This would allow a sensor manufacturer to prorate warranty settlements based on actual recorded sensor usage. The usage memory can also be used to record the conditions under which the sensor has been used. This information would allow a sensor manufacturer to see the conditions under which the sensor was used and to use this information for sensor development and/or marketing and for warranty issues should the user operate the sensor outside of its recommended limits.

The memory device can also include logic which monitors and controls the operation of the sensor. For example, some sensors can be damaged if they are heated too rapidly. The memory device can function to control how fast the sensor is heated.

The memory device can also include logic for detecting when the sensor is being used or has been used beyond its recommended limits, e.g., temperature, time, voltage, etc. The memory device can also include a mechanism for warning the user of the improper use or overuse.

5. Mechanism and Method for Compensating for Thermal Load Transients

During thermal load transients, ceramic sensors can experience periods where the sensor is not at the desired temperature. These temperature errors can reduce the accuracy of the sensor. Even with the use of a closed-loop temperature control system, significant errors in temperature can often occur. In order to accommodate for these errors in temperature, logic is provided for use with ceramic sensors which compensates for errors that can occur due to temperature transients that are not corrected by a closed-loop control system. By correcting for these errors in temperature, the accuracy of measurements from ceramic sensors is improved.

Figure 9:
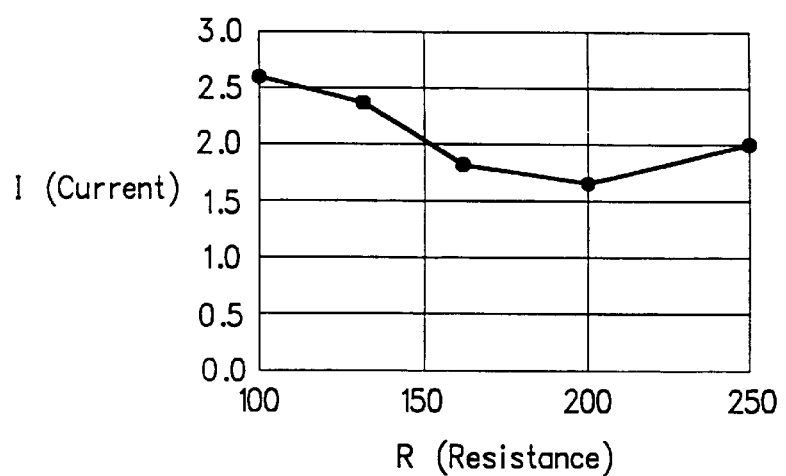
FIG. 9 is a graph plotting current from a ceramic sensor ($I_p$) as a function of temperature.

FIG. 9 is a graph plotting current ($I_p$) from a ceramic sensor (y axis) as a function of sensor impedence. The sensor is being exposed to a constant quantity of combustion emissions components and, as such, the current ($I_p$) should be constant. The temperature of a sensor can be determined based on the impedance of the sensor (x axis). Impedance is preferably measured near the time that the sensor's output signal(s) is measured.

According to one embodiment, the temperature of the sensor is measured based on the sensor's impedence. The sensor's output is then corrected based on the detected temperature if the sensor's temperature is found to deviate from the desired temperature, according to the following equation:

$$I_{corrected} = I_{measured} - I_{correction} = I_{measured} - G \times BR \times (R_{actual} - R_{target}) \quad \text{(VI)}$$

where:
  $I_{correction}$ is the correction to the pumping or dissociation currents measured in a ceramic exhaust gas sensor;
  G is the gain of the sensor at the particular operating point;
  BR is the slope of the $I_p$ versus sensor impedence curve in the vicinity of the target impedance ($R_{target}$) (BR is normalized to the average sensor gain);
  $R_{actual}$ is the actual sensor temperature (given here in terms of an impedence); and
  $R_{target}$ is the target sensor temperature (given here in terms of an impedence).

In an alternative embodiment, the gain of the sensor is modified by the actual sensor temperature according to the following equation:

$$G_{corrected} = G \times (1 + G \times MR \times (R_{actual} - R_{target}) \quad \text{(VI)}$$

where:
  MR is the sensitivity of the gain to a sensor temperature error (MR is normalized to the average sensor gain).

Figure 10B:
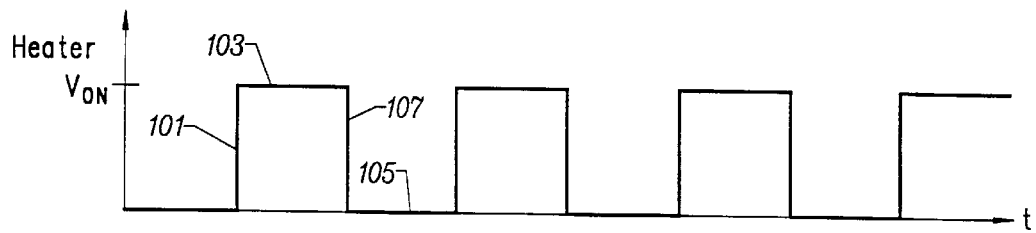
FIGS. 10A–10I illustrate a series of measuring timing patterns for enhancing the signal-to-noise ratio of the sensor.
Figure 10A:
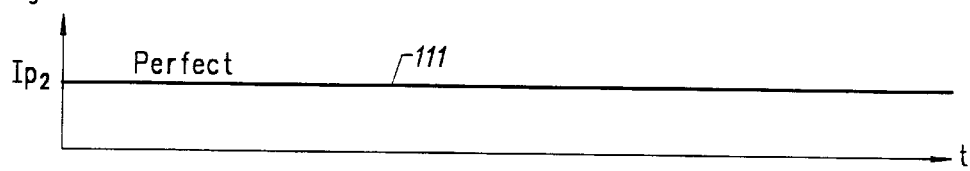

6. Mechanism and Method for Timing Sampling to Increase Signal-to-Noise Ratio A need exists to maximize the signal-to-noise ratio of sensors. FIG. 10A illustrates a noiseless signal ($I_{p2}$) in the sense that extraneous noise has been eliminated. Applicants have determined the existence of several sources of noise which mask this signal and have designed a timing pattern for taking sensor measurements which significantly reduces the effects of these sources of noise. By incorporating this timing pattern for taking measurements (i.e., sampling), the signal-to-noise ratio of a ceramic sensor was improved by a factor of 20.

Figure 10C:
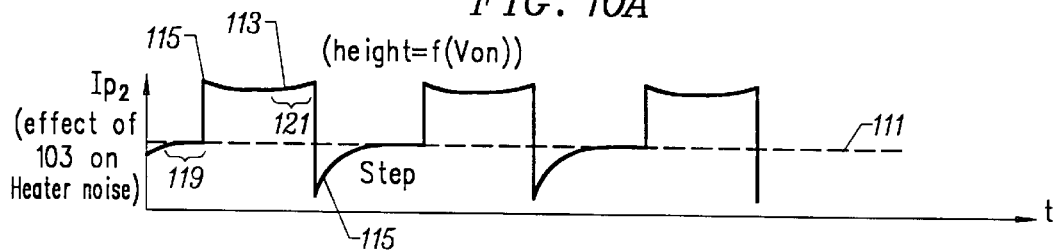

Applicants have detected the presence of leakage current from the heater of a ceramic sensor to its sensing element. FIG. 10B illustrates the cycling of voltage to the heater. As illustrated, the heater transitions 101 from an off state 105 to an on state 103 and transitions 107 from the on state 103 to the off state 105. FIG. 10C illustrates how the signal 111 illustrated in FIG. 10A is modified as a result of the leakage current. As can be seen in FIG. 10C, the leakage current causes the signal amplitude to increase 115 relative to signal 111 when the heater is on 103 and also introduces a noise effect 113 where the signal amplitude changes over time during an on or off state. This leakage current has been found to vary from sensor to sensor and change with sensor temperature.

To minimize the effect of heater leakage noise, measurements are preferably taken from the sensor when the heater is off or after the effects of the leakage current have reached steady state, most preferably just prior to turning the heater on. These time periods are illustrated in FIG. 10C as 119 and 121 respectively.

Figure 10D:
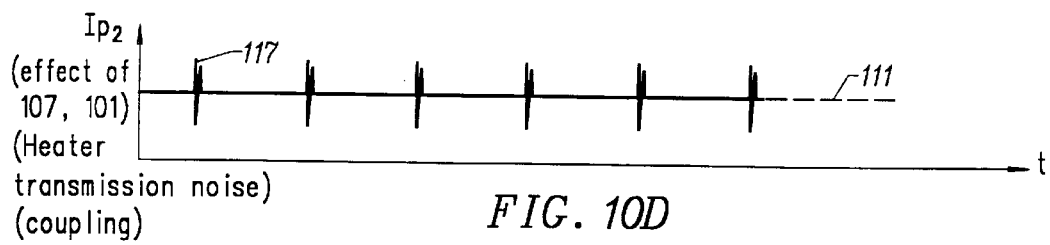

Applicants have also detected noise generated due to coupling between the heater wires and sensing element's wires. To minimize the effect of noise generated by coupling between the heater wires and the sensing element's wires, measurements are preferably taken just before transitions in the heater's voltage occurs. These transitions are illustrated in FIG. 10B as 101 and 107 and their noise effects are illustrated in FIG. 10D as 117.

Figure 10E:
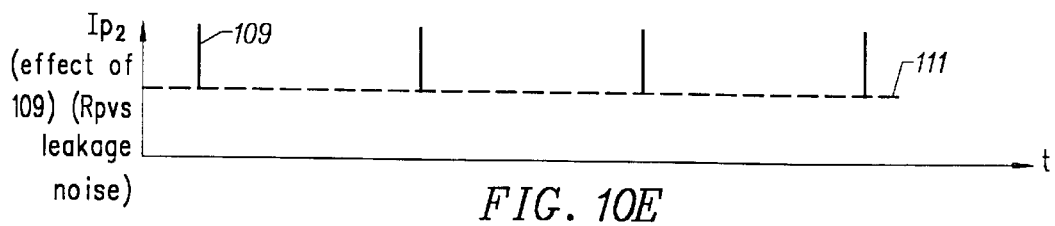

Another source of noise that has been detected is leakage current due to the use of an impedence method for measuring a sensor's temperature. FIG. 10E illustrates the timing of the impedance method where the noise effect is illustrated as 109. To minimize the effect of leakage current due to the impedence method, measurements are taken just before the impedence method is to occur.

A method is provided according to the present invention for taking sensor measurements based on a timing pattern which is designed to avoid the effects of these different sources of noise. This method can involve consideration of the heater's duty cycle on the timing pattern. For example, sensor measurements can be timed to not coincide with the delivery of current to the heater.

Figure 10F:
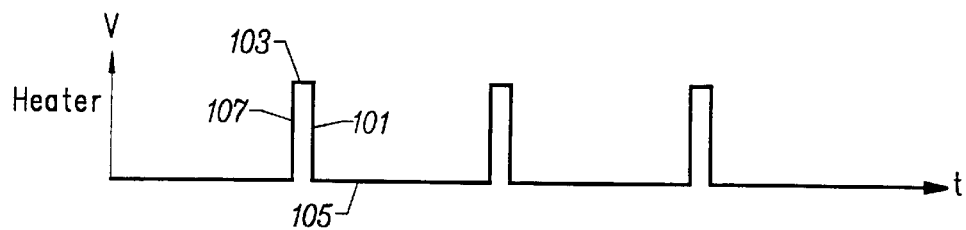
Figure 10G:
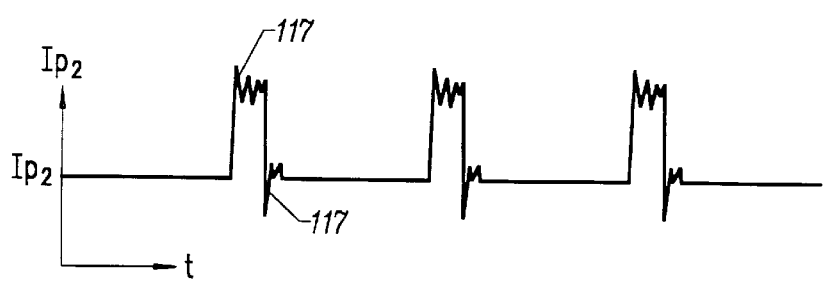

As illustrated in FIGS. 10F and 10G, at low heater duty cycles, noise 117 dominates the period when the heater is on 103. It is therefore preferred that sampling be done when the heater is off when the heater duty cycle is low.

Figure 10H:
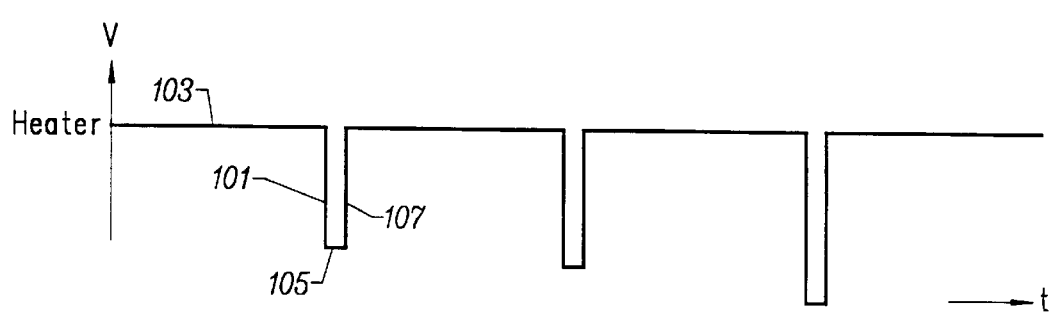
Figure 10I:
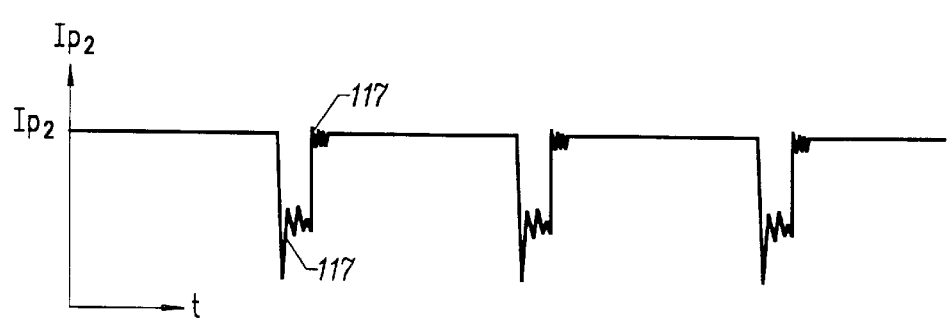

As illustrated in FIGS. 10H and 10I, at high heater duty cycles, noise 117 dominates the period 105 when the heater is off. It is therefore preferred that sampling be done when the heater is on when the heater duty cycle is high. In a preferred embodiment, the system in which the sensor is used includes logic for determining whether the heater duty cycle is low or high and for selecting the sampling times based on the duty cycle.

7. Method and System Involving Use of Regulated Voltage-type Heater with Ceramic Sensor Pulse-width modulated (PWM) heater controllers have traditionally been used with ceramic sensors. These heater controls serve to cycle the heater between on and off modes and thus include on-to-off and off-to-on transitions. This type of controller presents the operational disadvantages of having a long duty cycle at low voltages and exhibiting coupling between the heater wires and the sensing element wires during the on-to-off and off-to-on transitions of the heater.

According to this embodiment of the invention, a regulated voltage-type heater may be used with a ceramic sensor. Regulated voltage-type heaters have not used with ceramic sensors due to the greater complexity of their design and the observance of current leakage from the continuous heater voltage which affects the pumping and dissociation current readings. In this embodiment, the contribution to the pumping and/or dissociation current by the heater is measured at regular intervals and subtracted out in order to compensate for this source of noise. This enables more highly accurate measurements by allowing for more time for sample averaging as compared to PWM heater controllers. In addition, faster sensor start-up is enabled because the controller does not have to wait until the heater effects have decayed to steady-state values.

Figure 11:
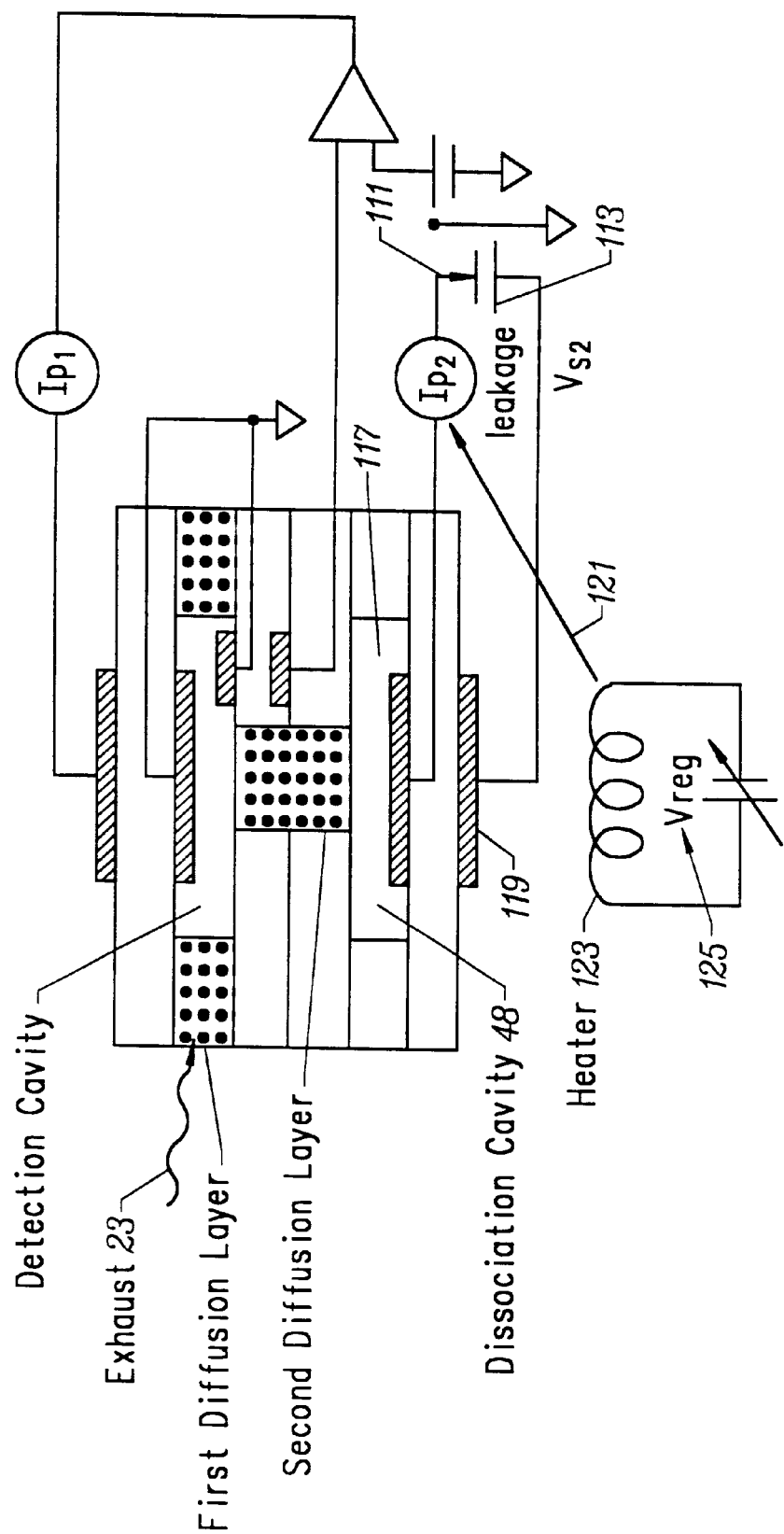
FIG. 11 illustrates a $NO_x$ sensor with a regulated voltage heater controller in a first configuration.
Figure 12:
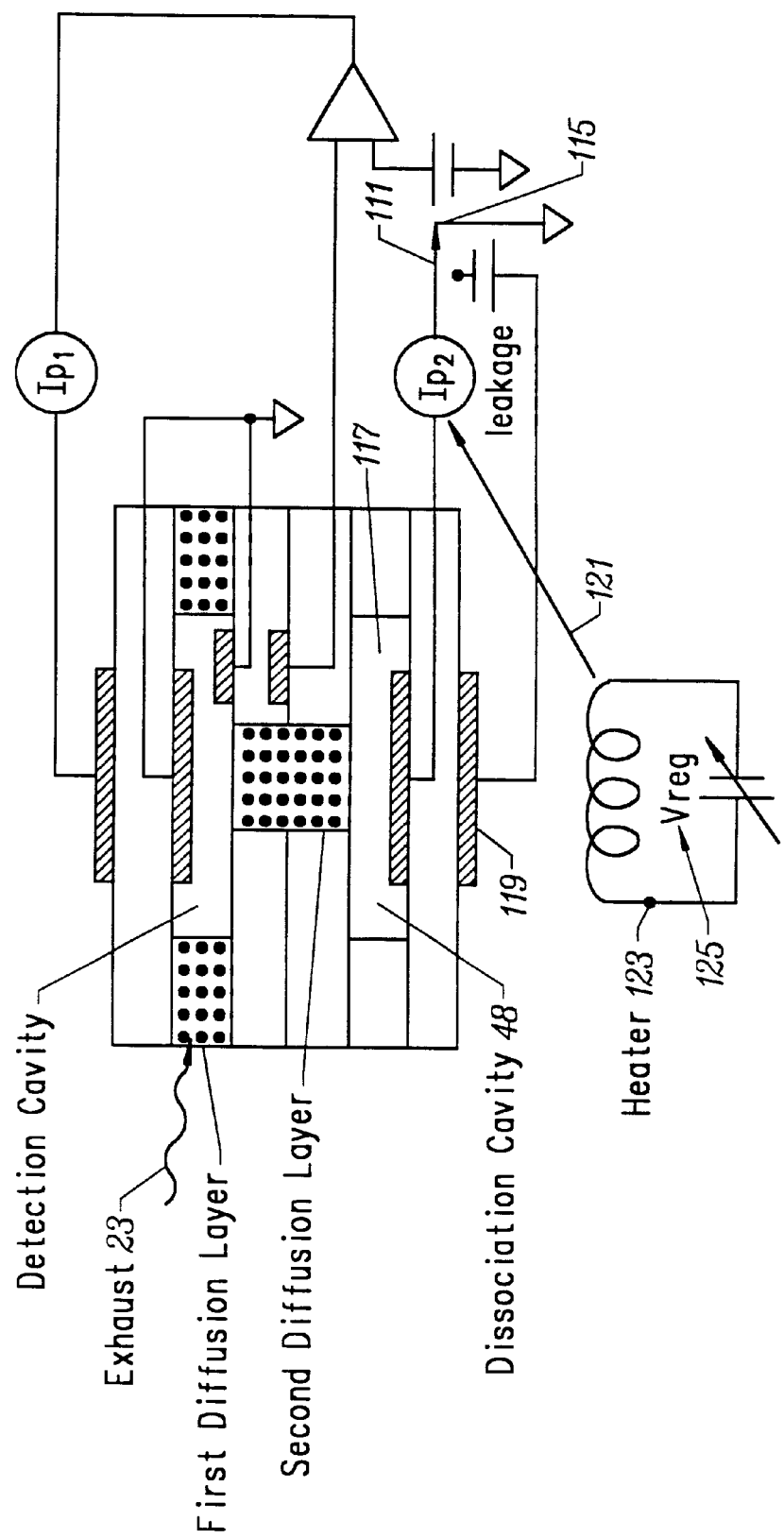
FIG. 12 illustrates a $NO_x$ sensor with a regulated voltage heater controller in a second configuration.

FIGS. 11 and 12 illustrate a $NO_x$ sensor with a regulated heater voltage 125. The temperature of the sensor can be measured by one of a variety of techniques including, for example, sensor impedance method, heater resistance, and thermocouple. Measurement of the temperature of the sensor is then used to modify the regulated voltage 125. The circuit alternatives between the two configurations, defined by the position of switch 111.

Configuration 1 is shown in FIG. 11. As illustrated in this figure, the dissociation voltage $V_{s2}$ 113 is applied across electrodes 117 and 119 causing the dissociation of oxygen-containing species in the dissociation cavity. In this configuration, the measured current $I_{p2}$ is due to the dissociation and leakage 121 of current from the heater 123.

Configuration 2 is shown in FIG. 12. As illustrated, the dissociation voltage $V_{s2}$ 113 is not applied across electrodes 117 and 119. In this configuration, the measured current $I_{p2'}$ is due only to leakage 121 from the heater 123.

The difference between the measured currents $I_{p2}$ and $I_{p2'}$ ($I_{p2}-I_{p2'}$) is independent of the effect of the heater and is used to determine the concentrations of components in the exhaust 23.

8. Method and Logic for Calibrating Sensors

For a two-cavity sensor, the basic relationship between the measured pumping current $I_{p2}$ 57 and the amount(s) of oxygen-containing species in the exhaust 23 is:

$$I_{p2}=I_{p2}=C+KX_i$$

where:

$I_{p2}$ = current due to pumping out $O_2$ from the second cavity (where the dissociation occurs) 48 that enters the second cavity from the first cavity 28 (the cavity prior to the cavity where the dissociation occurs) via the second diffusion layer 51 + current due to pumping out oxygen from the second cavity 48 that is created in second cavity from dissociating oxygen-containing species (ex. NOx, $CO_2$, $H_2O$). [VIII]

C is a constant;

K is a constant set by the propensity of the sensor to dissociate species i;

$X_i$ is the concentration of oxygen containing species in the exhaust 23;

It is standard practice to control the $O_2$ content of the first cavity to a constant amount and thus fix the first term in Equation VIII to a constant quantity C.

It is also standard practice to have conditions (ex. temperature, oxygen concentration, electrode composition) in the first cavity not conducive to the increase or reduction of the amount(s) of oxygen-containing species to be measured.

It is also standard practice to have conditions in the second cavity conditions (ex. temperature, oxygen concentration, electrode composition) conductive to the dissociation of the oxygen-containing species to be measured.

It is standard practice to choose the level of the dissociation voltage $V_{s2}$ 55 of the second cavity to select those oxygen-containing species to dissocate. At a low pumping voltage, primarily one species will dissociate. As the pumping voltage is increased, additional species will dissociate contributing to a greater $I_{p2}$. If a series of pumping voltages are used, the relative contribution of the different dissociated species, and hence the relative amounts of the dissociating species in the exhaust can be resolved.

The reasons for these standard practices is to make the first term in Equation VIII a constant and the second term a function of the oxygen-containing dissociating species, i.e.:

$$I_{p2}=C+K\times Xi \qquad [IX]$$

or:

$$Xi=(1/K)\times(I_{p2}-C)$$

or:

$$Xi=H\times(I_{p2}-C)$$

or:

$$Xi=H\times I_{p2}-A$$

where:
  $I_{p2}$=pumping current in the cavity where the dissociation occurs; and,
  C=a constant; and,
  K=is a constant set by the propensity of the sensor to dissociate species i; and,
  Xi=the concentration of dissociating oxygen-containing species i in the exhaust; and
  H=1/K; and,
  A=C/K.

Equation IX represents a prior art method for measuring the amount(s) of oxygen-containing species in an exhaust. It assumes that just one oxygen-containing species is dissociating. If multiple oxygen-containing species are dissociating then Xi in Equation IX will have to be replaced by $\Sigma Xi$ and different dissociation voltages $V_{s2}$ will have to be used to resolve the contributions of the different dissociating species to $I_{p2}$.

One shortcoming of Equation IX is that it is difficult if not impossible to control without error the amount of oxygen entering the second cavity. Therefore, due to imperfections in sensor design and control, C will vary with exhaust composition.

A second shortcoming of Equation IX is that it is difficult if not impossible to avoid reactions that increase or decrease the amounts(s) of oxygen-containing species prior-to their arrival in the second cavity (where they are measured). These reactions result in errors in measurements of the species. The magnitude of these errors can vary with exhaust composition because the rates of these reactions can vary with exhaust composition.

A third shortcoming of Equation IX is that it is difficult if not impossible to avoid the reactions of some oxygen freed by dissociation in the second cavity with molecules such as CO and HCs. These reactions result in errors in the measurements of the species. The magnitude of the errors can vary with exhaust composition because the amounts of the interfering species can vary with exhaust composition.

The present invention relates to a method for mitigating the effects of the above shortcomings on sensor accuracy by using a knowledge of the composition of the exhaust. The present invention also relates to sensors and sensor systems which incorporate logic for performing the method.

As can be seen from the graph illustrated in FIG. 2, the composition (i.e. amounts of CO, $O_2$, HC) of the exhaust of combustion devices is strongly influenced by the air-fuel ratio of the combustion device (ex. engine) producing the exhaust. The air-fuel ratio of the combustion device is a function of the pumping current $I_{p1}$ 53 of the first cavity via prior art.

Using these relationships, the following equation has been derived:

$$Xi=H(I_{p1})\times(I_{p2}-C(I_{p1})) \qquad [X]$$

where:
  H and/or C are not constants but rather functional relationships of the pumping current $I_{p1}$ of the first cavity. These relationships can be determined experimentally.

The pumping current $I_{p1}$ used in Equation X is preferably normalized to its value in a common and stable gaseous environment (ex. $I_{p1}$ in air). Accordingly, Equation X can be recast as:

$$Xi=H(I_{p1}/I_{p1\,n})\times(I_{p2}-C(I_{p1}/I_{p1\,n})) \qquad [XI]$$

The advantage of the construct of Equation XI is that the functional relationships between H or C and $I_{p1}$ do not degrade with sensor degradation. This is because the relationship between $I_{p1}$ and air-fuel ratio will scale with the relationship between $I_{p1n}$ and the common gaseous environment.

Using Equations X and XI, methods have been developed for determining the amounts of each oxygen-containing species (ex. $NO_x$, $CO_2$, $H_2O$) in a sample of combustion exhaust using any sensor that dissociates each species and uses the quantity of oxygen molecules produced by the dissociation as an indication of the amount of each species in the exhaust. One type of sensor which may be used in this method are two-cavity sensors, such as the one illustrated in FIG. 3. However, the method is not intended to be limited to two-cavity sensors. Rather, the method can be applied to a single-cavity, or three-cavity, or any other construct of sensor that uses dissociation to determine the amounts of oxygen-containing species.

According to one embodiment, the method is performed by applying a gaseous emission to the sensor; measuring a pumping current in a first cavity of the sensor which has a functional relationship to an air/fuel ratio of the gaseous emission; measuring a pumping current in a second cavity of the sensor which has a functional relationship to an amount of oxygen-containing species in the gaseous emission and the air/fuel ratio of the gaseous emission; and using a combination of the measured pumping currents of the first and second cavities to measure an amount of oxygen-containing species in the gaseous emission.

One advantage of the present method is a decrease in errors caused by variations in exhaust composition and sensor degradation, thus improving the sensor's accuracy. This method allows accurate calibration of the sensor using a simple combination of model gases. The use of model gases simplifies sensor calibration which makes the calibration less costly and quicker to perform, while retaining the accuracy of a calibration using actual combustion exhaust. This method permits sensor field calibration in a variety of environments which broadens the range of applications for the sensor.

Sensors are not conventionally calibrated in actual combustion exhaust. Instead, "model gases" of simplified compositions are generally used. A model gas is made by blending gases from tanks of specific molecules. For example, a simple model gas composition of $NO_x$, $O_2$, CO, and $N_2$ might be used to calibrate a sensor to measure $NO_x$. The problem with such calibration procedures is that it ignores the possible effects on the accuracy of the sensor of species that are in the exhaust but are not in the model gases. Such absent species, when in the exhaust, may either consume dissociated oxygen or cause more oxygen to be dissociated. The result being that a model gas calibration may not result in a calibration that is accurate in actual exhaust.

Since Equations IX, X, and XI are not limited to either model gases or actual exhaust, a relationship exists between the functions H and C determined in a model gas calibration and those determined in an exhaust gas calibration. For example, in one embodiment functions H and C determined in a model gas calibration are used to accurately calculate the amount of species i in an actual exhaust according to the equation:

$$Xi = G \times H \times (I_{p2} - M \times C) \quad [\text{XII}]$$

where:
G and M are corrections to H and C when going from measuring species i in a model gas to measuring species i in an exhaust; and
H and C are determined using model gases.

G, H, M, and C are preferably expressed as functions of $I_{p1}/I_{p1\ n}$. G and M are preferably determined once for a given construction of sensor and type of fuel combusted. If species i is to be measured in a model gas, G and M are set to 1. The advantage of the method of Equation XII is that it allows simple model gas calibrations to give exhaust gas calibration accuracy.

In a further embodiment of the present invention, the relationship expressed in Equation XII is used to enable field calibration of sensors. In general, it is desirable that instrumentation be able to be simply recalibrated while in use. Such calibrations are called "field calibrations". Field calibrations are typically two-point calibrations: one point at zero amount of the species to be measured and one point at a value greater than the maximum amount of the species to be measured. In order to perform field calibrations, Equation XII is modified to give:

$$Xi = G \times H \times SPAN \times (I_{p2} - M \times (C - ZERO)) \quad [\text{XIII}]$$

where:

$$SPAN = Xi / (G \times H \times (I_{p2} - M \times (C - ZERO)))$$

at the upper calibration point; and $$ZERO = C - I_{p2}/M \text{ when } Xi = 0.$$

According to Equation XIII, the result of field calibration is the determination of the quantities SPAN and ZERO to be used in Equation XIII. The advantage of this method is that field calibration can be performed in either model gases or actual exhaust. If field calibration is performed in model gases, G and M are set to 1 in the equations for SPAN and ZERO. If field calibration is performed in exhaust, G and M assume their values as determined.

According to one embodiment, the method of field calibration is performed by applying a gaseous emission having a known amount of oxygen-containing species to the sensor; measuring a pumping current in a first cavity of the sensor which has a functional relationship to an air/fuel ratio of a model gas; measuring a pumping current in a second cavity of the sensor which has a functional relationship to the amount of oxygen-containing species in the gaseous emission and the air/fuel ratio of the gaseous emission; and using a combination of the measured pumping currents of the first and second cavities and the known amount of oxygen-containing species in the gaseous emission to calibrate the sensor.

9. Method and Logic for Compensating for Rapid Emission Composition Transients

This embodiment provides a method for minimizing the effect of rapid emission composition transients on the accuracy of multiple cavity exhaust sensors while minimizing the associated additional costs.

Figure 13:
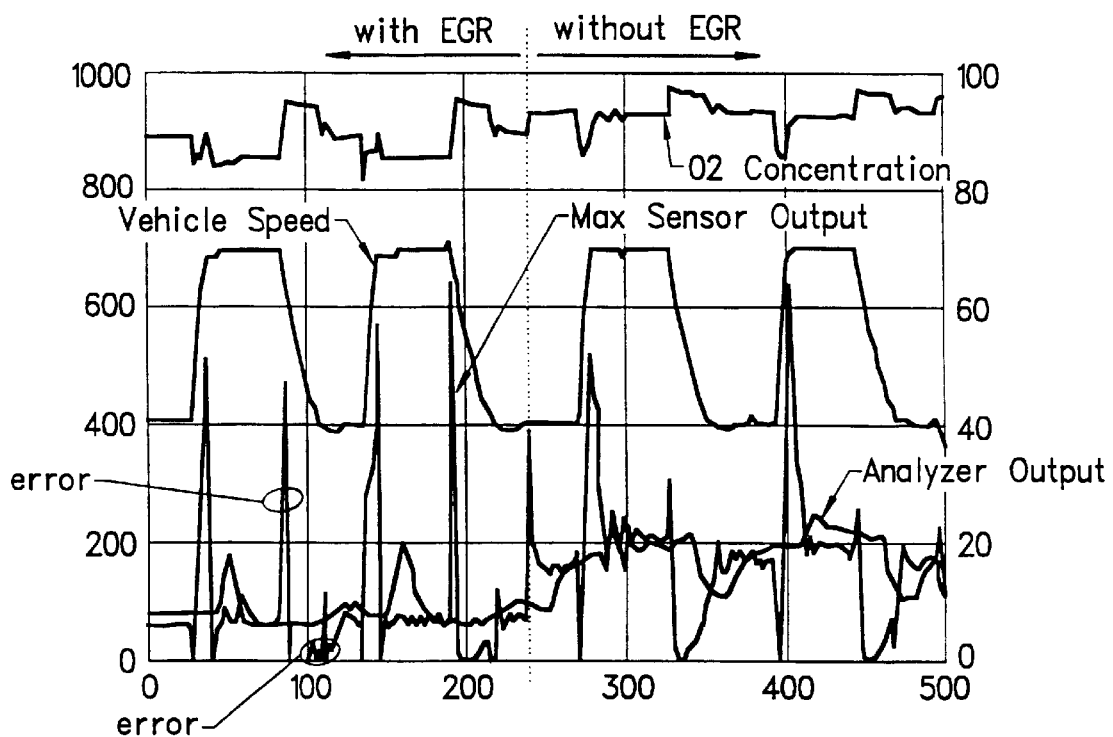
FIG. 13 illustrates signals from a dual-cavity ceramic exhaust sensor during engine load transients.

FIG. 13 illustrates signals from a two cavity exhaust sensor during engine emission composition transients. The sharp transients in measured $NO_x$ are not real but rather are caused by the delay in the first cavity's ability to control the level of oxygen in that cavity. Should the level of oxygen become greater or less than its target value, the perceived concentration of $NO_x$, as measured in the second cavity, becomes greater or less than it actually is.

The method of this embodiment involves controlling when $NO_x$ is and is not measured such that $NO_x$ is measured when the measurement is accurate and is not measured when the measurement is inaccurate.

Figure 14:
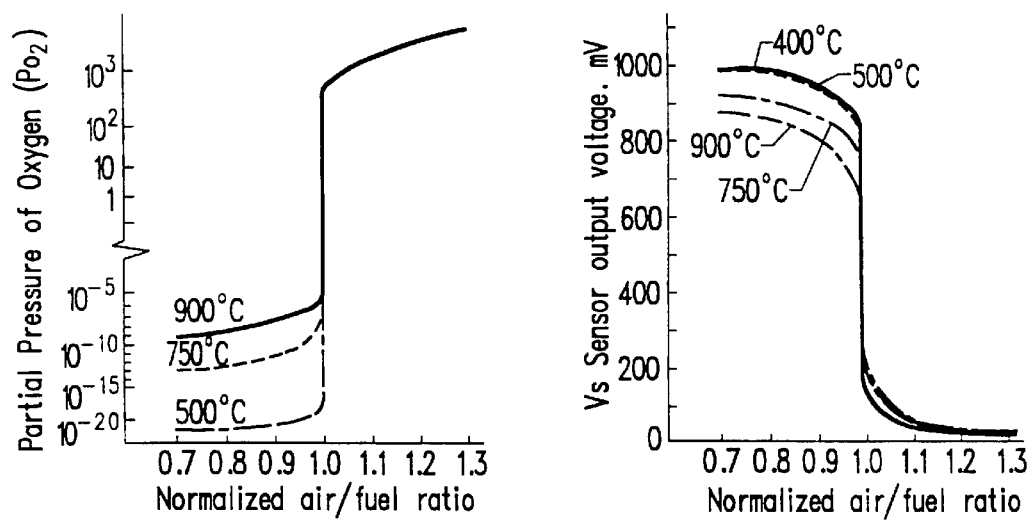
FIG. 14 is a plot of Vs.

As shown in FIGS. 14, $V_s$ has a very abrupt change in value with air/fuel ratio and oxygen concentration in the vicinity of the stoichiometric point. Multiple cavity sensors such as two-cavity sensors are typically operated on or near the stoichiometric point and are used to control the concentration of oxygen in the first cavity to a target value. During rapid emission composition transients, the concentration of oxygen in the first cavity will go off-target and this will be reflected in an off-target $V_s$ value. This embodiment uses $V_s$ information to control the compensation logic.

Figure 15:
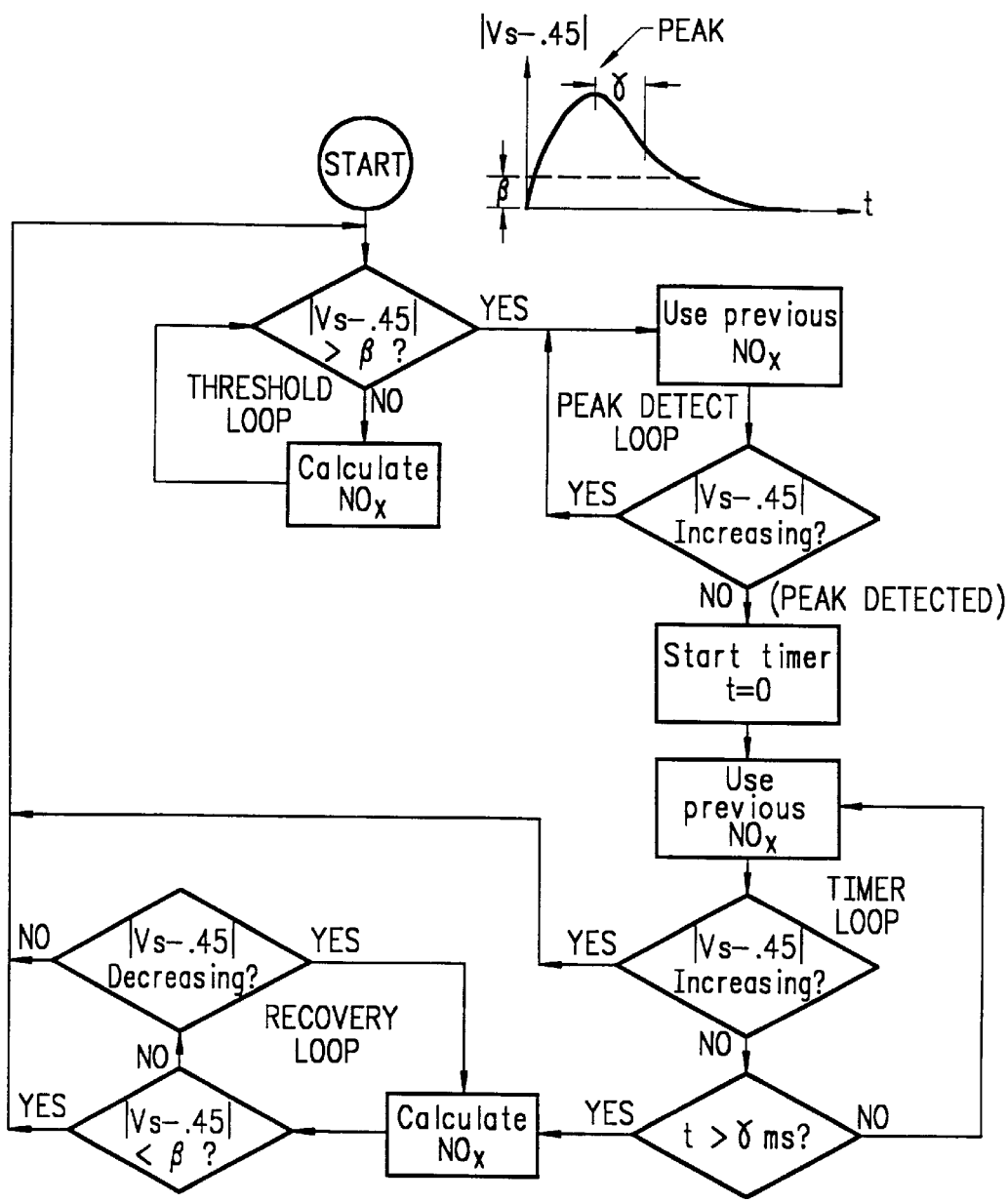
FIG. 15 illustrates a software flowchart for the technique.

FIG. 15 illustrates a software flowchart for the technique. The software flowchart contains four conditional loops: threshold loop, peak detect loop, timer loop, and recovery loop.

The threshold loop determines whether or not to compensate the measured $NO_x$ value based on a difference between the value of $V_s$ and the target value, shown in the flowchart to be 0.45 V. When Vs diverges from the target value by more than a predetermined value, shown in the flowchart as β, then the peak detect loop is entered. In the peak detect loop, the previously determined value of $NO_x$ is used instead of subsequent samples. Within the peak detect loop, a maximum deviation of Vs is monitored for. When a maximum deviation of Vs relative to the target value is reached, a timer is started for a predetermined time period, shown as y, and the timer loop is entered.

For the predetermined time period, the previously determined value for $NO_x$ is used until either the predetermined time period expires or the difference between Vs and the target value increases. When the time period expires, the recovery loop is entered. Meanwhile, if the difference between Vs and the target value is found to be increasing, the threshold loop is entered.

In the recovery loop, the sampled $NO_x$ value is used until Vs deviates from the target value less than β or Vs begins to diverge from its target value. When either of these events occur, the threshold loop is entered.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for quantifying a component of a gas emission comprising:
    taking a sensor including a first pumping cell which includes first electronics which maintain a first chemical environment adjacent the first pumping cell and measures a first pumping current, and
    a second pumping cell which includes second electronics which maintain a second chemical environment adjacent the second pumping cell and measures a second pumping current;
    contacting the sensor with a gas emission;
    measuring the first and second pumping currents; and
    quantifying a component of the gas emission using the equation $$Xi = H(I_{p1}) \times (I_{p2} - C(I_{p1}))$$

where
    Xi is the concentration of the component being quantified;
    $I_{p1}$ is the first pumping current;
    $I_{p2}$ is the second pumping current;
    $H(I_{p1})$ is a constant; and
    $C(I_{p1})$ is a non-constant function of the first pumping current.

2. A method according to claim 1 wherein the sensor is an oxygen-containing species detection sensor.

3. A method according to claim 1 wherein the sensor is a $NO_x$ sensor.

4. A method according to claim 1 wherein the component measured is an oxygen-containing species.

5. A method according to claim 1 wherein the component measured is $NO_x$.

6. A method according to claim 1 wherein the component measured is $CO_2$.

7. A method according to claim 1 wherein the component measured is $H_2O$.

8. A method according to claim 1 wherein the component measured is CO.

9. A method according to claim 1 wherein the component measured is $O_2$.

10. A method according to claim 1 wherein an electrode of the first pumping cell has a different catalytic activity than an electrode of the second pumping cell.

11. A method according to claim 1 wherein at least one of the first and second pumping cells pump oxygen.

12. A system for quantifying a component of a gas emission comprising:
    a sensor comprising:
    a first pumping cell which includes first electronics which maintain a first chemical environment adjacent the first pumping cell and measures a first pumping current;
    a second pumping cell which includes second electronics which maintain a second chemical environment adjacent the second pumping cell and measures a second pumping current;
    a mechanism which measures the first and second pumping currents; and
    a mechanism which quantifies a component of the gas emission using the equation $$Xi = H(I_{p1}) \times (I_{p2} - C(I_{p1}))$$

where
    Xi is the concentration of the component being quantified;
    $I_{p1}$ is the first pumping current;
    $I_{p1}$ is the second pumping current;
    $H(I_{p1})$ is a constant; and
    $C(I_{p1})$ is a non-constant; function of the first pumping current.

13. A system according to claim 12 wherein the sensor is an oxygen-containing species detection sensor.

14. A system according to claim 12 wherein the sensor is a $NO_x$ sensor.

15. A system according to claim 12 wherein the component measured in an oxygen-containing species.

16. A system according to claim 12 wherein $H(I_{p1})$ and $C(I_{p1})$ are for measuring $NO_x$.

17. A system according to claim 12 wherein $H(I_{p1})$ and $C(I_{p1})$ are for measuring $CO_2$.

18. A system according to claim 12 wherein $H(I_{p1})$ and $C(I_{p1})$ are for measuring $H_2O$.

19. A system according to claim 12 wherein $H(I_{p1})$ and $C(I_{p1})$ are for measuring CO.

20. A system according to claim 12 wherein $H(I_{p1})$ and $C(I_{p1})$ are for measuring $O_2$.

21. A system according to claim 12 wherein at least one of the first and second pumping cells pump oxygen.

* * * * *